(12) United States Patent
Damadian et al.

(10) Patent No.: US 10,799,141 B1
(45) Date of Patent: Oct. 13, 2020

(54) IMAGE DIRECTED CEREBROSPINAL FLUID (CSF) FLOW DETERMINATION METHOD AND SYSTEM

(71) Applicant: Fonar Corporation, Melville, NY (US)

(72) Inventors: Raymond V. Damadian, Woodbury, NY (US); Robert Wolf, Medford, NY (US)

(73) Assignee: Fonar Corporation, Melville, NY (US)

( * ) Notice: Subject to any disclaimer, the term of this patent is extended or adjusted under 35 U.S.C. 154(b) by 610 days.

(21) Appl. No.: 15/222,450

(22) Filed: Jul. 28, 2016

Related U.S. Application Data

(60) Provisional application No. 62/197,903, filed on Jul. 28, 2015.

(51) Int. Cl.
| | | |
|---|---|---|
| *A61B 5/055* | (2006.01) | |
| *A61B 5/00* | (2006.01) | |
| *G06K 9/46* | (2006.01) | |
| *G06T 7/246* | (2017.01) | |
| *G06T 7/12* | (2017.01) | |
| *G06T 7/136* | (2017.01) | |
| *G01R 33/563* | (2006.01) | |
| *G01R 33/56* | (2006.01) | |

(52) U.S. Cl.
CPC ............ *A61B 5/055* (2013.01); *A61B 5/0042* (2013.01); *G01R 33/5608* (2013.01); *G01R 33/56308* (2013.01); *G06K 9/4647* (2013.01); *G06T 7/12* (2017.01); *G06T 7/136* (2017.01); *G06T 7/248* (2017.01); *G06T 2207/10088* (2013.01); *G06T 2207/20104* (2013.01); *G06T 2207/30012* (2013.01)

(58) Field of Classification Search
None
See application file for complete search history.

(56) References Cited

U.S. PATENT DOCUMENTS

| | | | |
|---|---|---|---|
| 6,369,571 B1 | 4/2002 | Damadian et al. | |
| 6,414,490 B1 | 7/2002 | Damadian et al. | |
| 6,677,753 B1 | 1/2004 | Danby et al. | |
| 8,401,162 B2 | 3/2013 | Sakata et al. | |
| 8,401,612 B1 * | 3/2013 | Chu ..................... | A61B 5/4058 5/601 |

(Continued)

OTHER PUBLICATIONS

Damadian et al., The Possible Role of Cranio-Cervical Trauma and Abnormal CSF Hydrodynamics in the Genesis of Multiple Sclerosis, Physiol. Chem. Phys. & Med. NMR, 41, pp. 1-17, Sep. 2011.

*Primary Examiner* — Jonathan Cwern
(74) *Attorney, Agent, or Firm* — Lerner, David, Littenberg, Krumholz & Mentlik, LLP

(57) ABSTRACT

In one aspect, the present disclosure describes a method for detecting cerebrospinal fluid (CSF) flow of a subject in which magnetic resonance imaging signals of a selected region of interest of the subject's anatomy are acquired. Preferably, the selected region of interest comprises the cerebro-spinal anatomy. A central location of the selected region of interest of the subject's anatomy is determined and used to determine a mean intensity value associated with image pixels of the central location. The mean intensity value is then used to establish interior and exterior outlines of the the selected region of interest of the subject's anatomy so that the CSF flow within the interior and exterior anatomical outlines may be measured or detected.

16 Claims, 5 Drawing Sheets

(56) References Cited

U.S. PATENT DOCUMENTS

| | | |
|---|---|---|
| 8,834,387 B2 | 9/2014 | Platt |
| 9,649,047 B1 | 5/2017 | Damadian et al. |
| 2013/0289387 A1* | 10/2013 | Shiodera ................ A61B 5/055 600/419 |
| 2015/0080704 A1* | 3/2015 | Burke .................. A61N 5/1049 600/411 |

* cited by examiner

IMAGE DIRECTED CEREBROSPINAL FLUID (CSF) FLOW DETERMINATION METHOD AND SYSTEM

CROSS-REFERENCE TO RELATED APPLICATIONS

The present application claims the benefit of the filing date of U.S. Provisional Patent Application No. 62/197,903 filed Jul. 28, 2015, the disclosure of which is hereby incorporated herein by reference.

TECHNICAL FIELD

The present disclosure relates to magnetic resonance imaging apparatus, systems and methods and procedures for improved quantification of Cerebro-Spinal Fluid ("CSF") flow anywhere in the cerebro-spinal anatomy, e.g., within the ventricles, the cerebral acqueduct (or acqueduct of Sylvius), spinal canal, the sub-arachnoid space, the epidural space, the cerebello-medullary cistern, foramen of Monro, foramen of Magendie, foramen magnum, etc., i.e., where it is flowing.

BACKGROUND

In magnetic resonance imaging, an object to be imaged such as, for example, a body of a human subject, is exposed to a strong, substantially constant static magnetic field. Radio frequency excitation energy is applied to the body, and this energy causes the spin vectors of certain atomic nuclei within the body to rotate or "precess" around axes parallel to the direction of the static magnetic field. The precessing atomic nuclei emit weak radio frequency signals during the relaxation process, referred to herein as magnetic resonance signals. Different tissues produce different signal characteristics. Furthermore, relaxation times are the major factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. In addition, magnetic resonance imaging can obtain images of soft tissues and other features within the body which are not readily visualized using other imaging techniques. Accordingly, magnetic resonance imaging has been widely adopted in the medical and allied arts.

Several factors impose significant physical constraints in the positioning of patients and ancillary equipment in MRI imaging. Many MRI magnets use one or more solenoidal superconducting coils to provide the static magnetic field arranged so that the patient is disposed within a small tube running through the center of the magnet. The magnet and tube typically extend along a horizontal axis, so that the long axis or head-to-toe axis of the patient's body must be in a horizontal position during the procedure. Moreover, equipment of this type provides a claustrophobic environment for the patient. Iron core magnets have been built to provide a more open environment for the patient. These magnets typically have a ferromagnetic frame with a pair of ferromagnetic poles disposed one over the other along a vertical pole axis with a gap between them for receiving the patient. The frame includes ferromagnetic flux return members such as plates or columns extending vertically outside of the patient-receiving gap. A magnetic field is provided by permanent magnets or electromagnetic coils associated with the frame. A magnet of this type can be designed to provide a more open environment for the patient. However, it is still generally required for the patient to lie with his or her long axis horizontal.

Recently, ferromagnetic frame magnets having horizontal pole axes have been developed. As disclosed, for example, in commonly assigned U.S. Pat. Nos. 6,414,490 and 6,677,753, the disclosures of which are incorporated by reference herein, a magnet having poles spaced apart from one another along a horizontal axis provides a horizontally oriented magnetic field within a patient-receiving gap between the poles. Such a magnet can be used with a patient-positioning device including elevation and tilt mechanisms to provide extraordinary versatility in patient positioning. For example, where the patient positioning device includes a bed or similar device for supporting the patient in a recumbent position, the bed can be tilted and/or elevated so as to image the patient in essentially any position between a fully standing position and a fully recumbent position, and can be elevated so that essentially any portion of the patient's anatomy is disposed within the gap in an optimum position for imaging. As further disclosed in the previously mentioned patents, the patient positioning device may include additional elements such as a platform projecting from the bed to support the patient when the bed is tilted towards a standing orientation. Still other patient supporting devices can be used in place of a bed in a system of this type. For example, a seat may be used to support a patient in a sitting position. Thus, magnets of this type provide extraordinary versatility in imaging.

Cerebrospinal fluid ("CSF") is a clear body fluid found in the brain and spine. It provides mechanical and immunological protection to the brain, as well as cerebral autoregulation of cerebral blood flow. While references by ancient physicians, e.g., Hippocrates and Galen, to "water" or "liquid" surrounding or within the brain, suggest awareness of CSF for millennia, in recent years its study has taken on renewed importance. For example, in a Sep. 20, 2011 paper entitled "The Possible Role of Cranio-Cervical Trauma and Abnormal C SF Hydrodynamics in the Genesis of Multiple Sclerosis" and published in Physiological Chemistry and Physics and Medical NMR, Vol. 41: 1-17, Damadian and Chu uncovered a key set of new observations regarding the possible relationship between CSF flow and Multiple Sclerosis (MS). In their work, Damadian and Chu conducted MRI studies of CSF flow in several patients observing that the "obstruction to CSF outflow would result in an increase in ventricular CSF pressure (ICP) which in turn could result in 'leakage' of cerebrospinal fluid and its content . . . ." The importance of understanding the relationship between CSF flow, velocity, volume, etc. and a variety of physical and/or neurological maladies cannot be overstated. As such, systems and methods that can better enable that understanding are extremely important to the medical profession.

As such, needs arise that require improvement in MRI technology, including software and related hardware. For example, while MRI captures tissue contrasts, improvements are needed to enable real time quantification of CSF flow in the cerebro-spinal anatomy.

SUMMARY

The present disclosure is directed to methods and system or apparatus that detect and/or determine cerebrospinal fluid (CSF) flow within a selected region of anatomy. In one aspect, the method detects CSF flow of a subject. The method comprises acquiring magnetic resonance imaging signals of a selected region of interest of the subject's anatomy, the selected region of interest comprising the cerebro-spinal anatomy; determining a central location of the cerebro-spinal anatomy; and processing the acquired magnetic resonance imaging signals to determine a mean intensity value associated with the cerebro-spinal anatomy by calculating a three-by-three neighborhood average associated with image pixels of the central location. This method may further comprise comparing the mean intensity values to intensity values of pixels that make up the cerebro-spinal anatomy to determine interior and exterior anatomical outlines of the cerebro-spinal anatomy; and detecting the CSF flow within the interior and exterior anatomical outlines.

In another aspect a system is provided. The system comprises an apparatus for acquiring magnetic resonance imaging signals of a selected region of interest of the subject's anatomy, the apparatus having a pair of magnetic poles spaced apart along a horizontal direction parallel to a support surface of the apparatus, the magnetic poles configured to create a magnetic field in the horizontal direction, the apparatus capable of accommodating the subject between the poles in an upright position; a memory storing instructions; a processor programmed using the instructions and configured to: receive the acquired magnetic resonance signals, determine a center location of the selected region of interest of the subject's anatomy using the acquired magnetic resonance signals, calculate a mean intensity value associated with the selected region of interest of the subject's anatomy using a three-by-three neighborhood average associated with image pixels of the center location, compare the mean intensity values to intensity values of pixels that make up the selected region of interest of the subject's anatomy to determine interior and exterior anatomical outlines of the subject's anatomy, and measure the CSF flow within the interior and exterior anatomical outlines.

In another aspect a method for detecting and creating magnetic resonance imaging anatomical outlines of a subject is provided. The method comprises acquiring magnetic resonance imaging signals of a selected region of interest of the subject's anatomy; processing the magnetic resonance imaging signals to determine image pixel intensity of one or more pixels associated with the selected region of interest; and determining anatomical outlines associated with the selected region of interest by comparing the image pixel intensity of the one or more pixels to a threshold value.

In yet another aspect a for determining cerebro-spinal fluid (CSF) flow of a subject is disclosed. The method comprises acquiring magnetic resonance imaging signals of a selected region of interest of the subject's anatomy; receiving as input to a computing device one or more anatomical outlines that define a portion of the selected region; processing pixel intensity data of one or more pixels associated with the portion of the selected region defined by the anatomical outlines to determine a cross-sectional area; and determining anatomical outlines associated with the selected region of interest by comparing the image pixel intensity of the one or more pixels to a threshold value.

One or more of the foregoing aspects may further comprise designating pixels with intensity values 50% above the mean intensity value as part of the part of an interior anatomical outline or designating pixels with intensity values 25% below the mean intensity value as part of the part of an external anatomical outline.

In addition, the cerebro-spinal anatomy comprises the spinal cord and flowing CSF surrounding the spinal cord. Further still, the cerebro-spinal anatomy may be selected from the group consisting of ventricles, cerebral acqueduct (or acqueduct of Sylvius), spinal canal, the sub-arachnoid space, the epidural space, the cerebello-medullary cistern, foramen of Monro, foramen of Magendie, and foramen magnum.

In addition, the comparison may comprise comprises performing a radial sweep through the one or more pixels about the central location of the spinal cord.

Further still, the magnetic resonance imaging signals of the selected region of interest of the subject's anatomy may be acquired while the subject is in an upright position. In this regard, the upright position may be selected from the group consisting of a sitting position and a standing position.

Further still, the pixels that make up the images may be derived from T2-weighted magnetic resonance imaging signals.

In addition, determining further may comprise determining the outlines a mean intensity value associated with the spinal cord by calculating a three-by-three neighborhood average of the one or more pixels associated with a central location of the spinal cord. Further still, determining may further comprise determining an anatomical outline around the spinal cord by comparing the image pixel intensity of the one or more pixels associated with the central location of the spinal cord with the mean intensity value.

Additionally, the method or system may further comprise displaying the selected region of interest as an image on a display or a display for doing same. The anatomical outlines may then be drawn on the display and comprise input to a processor.

DETAILED DESCRIPTION

The description to follow provides enabling but non-limiting examples of the various aspects of the present disclosure. From these non-limiting examples one skilled in the art will appreciate that the disclosed methods and systems may be modified without departing from the teachings and scope of the claimed invention.

Figure 1:
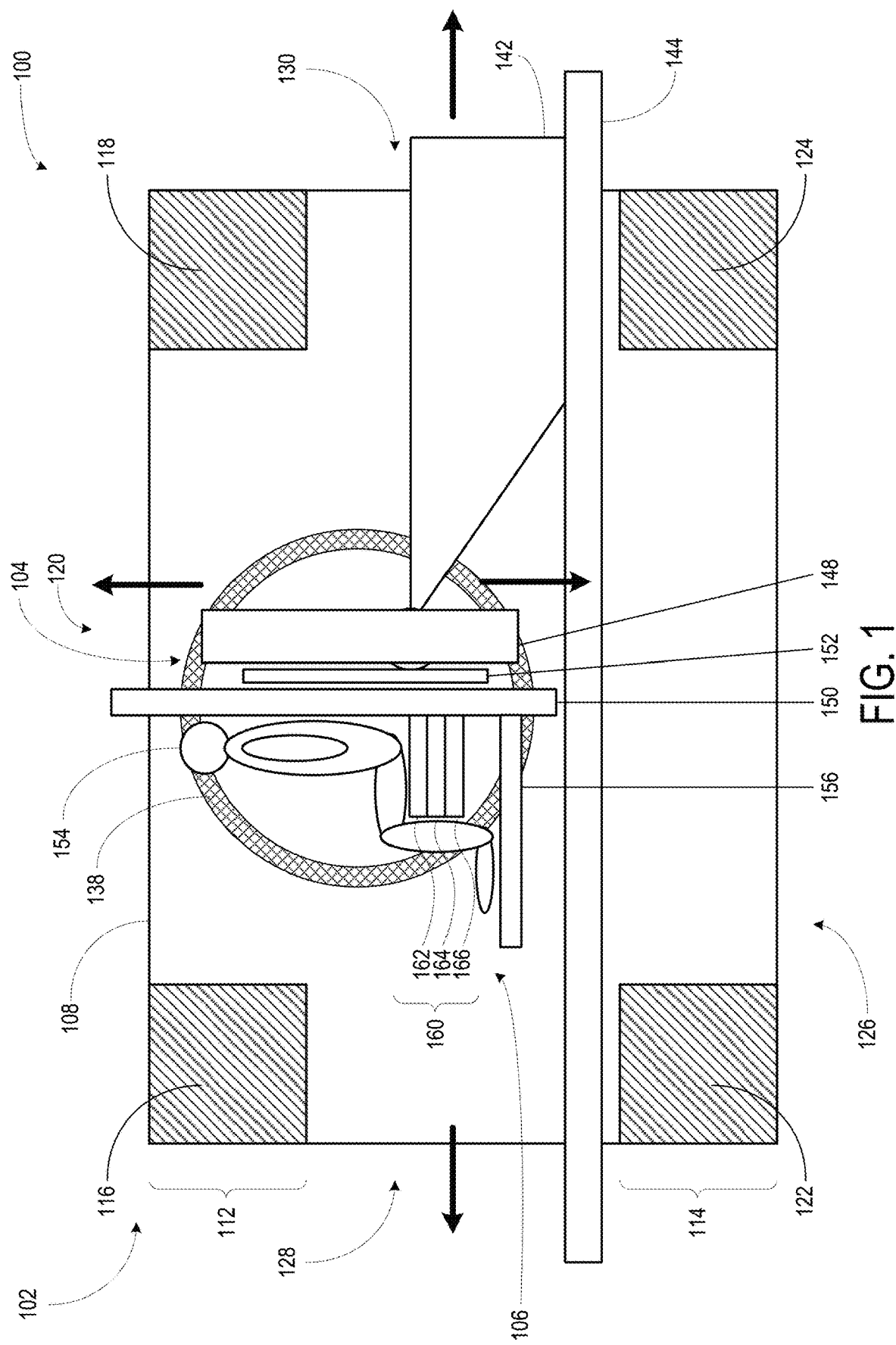
FIG. 1 illustrates an exemplary MRI apparatus for imaging a subject according to aspects of this disclosure.

FIG. 1 illustrates an exemplary MRI apparatus 100 for imaging a subject according to aspects of the disclosure. In one embodiment, the MRI apparatus 100 includes a magnet having a ferromagnetic frame 102, a magnetic flux generator 104, and a patient handling system 106. The ferromagnetic frame 102 includes a first side wall 108 and a second side wall. The side walls extend vertically. As FIG. 1 is a sectional view of the MRI apparatus 100, FIG. 1 does not show the second side wall or any of its associated structures for clarity. The second side wall would include all the components necessary to complete the path for a magnetic circuit or loop, e.g., a corresponding pole or an electromagnetic coil assembly to that shown in FIG. 1 with reference numeral 138, etc.

The ferromagnetic frame 102 may also include a top flux return structure 112 and a bottom flux return structure 114. The top flux return structure 112 may include two columnar structures 116 and 118. Between these two columnar structures, a top opening 120 is defined. Similarly, the bottom flux return structure 114 may include two columns 122 and 124 that together define a bottom opening 126. Thus, the side walls and the flux return members 112 and 114 form a rectilinear structure, with the top flux return structure 112 constituting the top wall of the rectilinear structure, the bottom flux return structure 114 constituting the bottom wall of the rectilinear structure and the side walls forming the side walls of the rectilinear structure. The frame 102 defines a front patient opening 128 on one side of the frame and a similar back patient opening 130 on the opposite side of the frame.

The ferromagnetic frame further includes a first magnetic pole and a second magnetic pole. The first magnetic pole extends from the first side wall 108 towards the second side wall and the second magnetic pole extends from the second side wall towards the first side wall 108. The magnetic poles are generally cylindrical and are coaxial with one another on a common horizontal polar axis. Between the magnetic poles is a gap accessed by the front patient opening 128, the back patient opening 130, the top opening 120 or the bottom opening 126.

The magnetic flux generator 104 includes a first electromagnetic coil assembly 138 magnetically coupled to ferromagnetic frame 102, proximate to side 108, and parallel to side 108. The magnetic flux generator 104 also includes a second electromagnet coil assembly (not shown) magnetically coupled to ferromagnetic frame 102, proximate to the second side wall, and parallel to the second side wall. As previously noted, these electromagnetic coil assemblies 138 and 140 may be either resistive or superconductive. Alternatively, the magnetic flux generator 104 may be a permanent magnet. The magnetic flux generator 104 may be configured to emit a magnetic field $B_0$ along one or more axes. The magnetic flux generator 104 may also include one or more gradient coils (not shown) for inducing a gradient in the $B_0$ magnetic field. The $B_0$ magnetic field generally extends horizontally parallel to support surface of the apparatus from one side wall to the other. The support surface will generally be the floor of a building or facility housing the apparatus 100.

The apparatus 100 may further include a patient support assembly 106 including a chair or seat assembly 160 on which a patient is capable of sitting. The patient handling system 106 is capable of three degrees of motion. The patient handling system further supports positioning of a patient in the Trendelburg and reverse-Trendelburg orientations. Generally, the degrees of motion allow for positioning of the patient in a variety of orientations or positions. The patient handling system 106 may include a carriage 142 mounted on rails 144. The carriage 142 may move linearly back and forth along the rails 144. The rails 144 typically do not block the bottom open space 126.

A generally horizontal pivot axis is mounted on carriage 142. An elevator frame 148 is mounted to the pivot axis. The carriage 142 is operable to rotate the elevator frame 148 about the pivot axis. A patient support 150 is mounted on the elevator frame 148. The patient support 150 may be moved linearly along the elevator frame 148 by an actuator 152. Thus, a patient 154 can be positioned with a total of three degrees of freedom, or along three axes of movement. Specifically, the patient handling system 106 can move a patient 154 in two linear directions and also rotate patient 154 around an axis. The solid black arrows of FIG. 1 show various axes of movement possible with the patient handling system 106. Note that often the rails 108 are mounted such that portions of patient 154 may be positioned below the rails through bottom open space 126.

The apparatus 100 may be configured such that the seat assembly 160 is not present. In that configuration, the patient would then be allowed to stand on the support 156. Allowing the patient to sit or stand, or more generally to remain in an upright position during image, has many advantages. For example, blood and CSF flow will be different in the upright position than in a recumbent position and may reveal. In addition, upright imaging of CSF flow may reveal abnormal conditions.

In making MRI measurements, the patient is fitted with an antenna coil that receives magnetic resonance signals from the region of interest of the subject's anatomy being imaged. Such antennas are placed at on or proximate the patient and may include a variety of geometries that maximize the signal strength and signal-to-noise (S/N) ratios of the magnetic resonance signals emitted by the anatomy of interest. Such antennas may include head coils to capture image signals associated with the head, neck or upper spine. Other antennas may include coils that are place proximate the back or spinal column. As another example, the patient support assembly 106 may include a seat assembly 160 may include a quadrature coil arrangement. In particular, the seat assembly 160 may include a seat or sitting surface 166, an enclosure 162 containing a contoured quadrature coil, and a cushion 164. The enclosure 162, which is shown as being adjacent to patient 154, may then the contoured quadrature coil having a normal vector transverse to the horizontal pole axis of the magnetic poles of the MRI apparatus 100, and thus transverse to the magnetic field vector parallel to the horizontal pole axis.

Additional views and disclosure of an MRI apparatus of the type discussed above may be found by reference to U.S. Pat. No 6,677,753, the disclosure of which is incorporated herein by reference. Alternative embodiments of the MRI apparatus also include those discussed in U.S. Pat. No. 6,414,490, the disclosure of which is also incorporated by reference. In addition, the magnetic resonance image apparatus does not necessarily need to include ferromagnetic frames or poles. For example, an apparatus such as that disclosed in commonly assigned U.S. Pat. No. 8,384,387, the disclosure of which is incorporated by reference herein, may comprise the magnetic resonance imaging apparatus in accordance with the various aspects of the present invention.

Figure 2A:
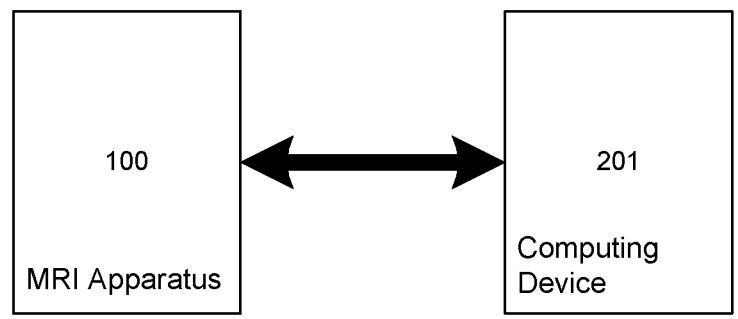
FIG. 2A illustrates a system in accordance with an aspect of this disclosure.

Turning now to FIG. 2A, there is shown a high level block diagram of a system 200 that includes the apparatus 100 and a computing device 201. The computing device 201 is programmed using instructions that cause it to receive magnetic resonance imaging signals from the apparatus 100 and process those signals to determine an outline associated with the anatomy of interest, and use the outline to control detection and/or measurement of CSF flow in an area adjacent to the anatomy of interest or otherwise associated with the subject's anatomy.

Figure 2B:
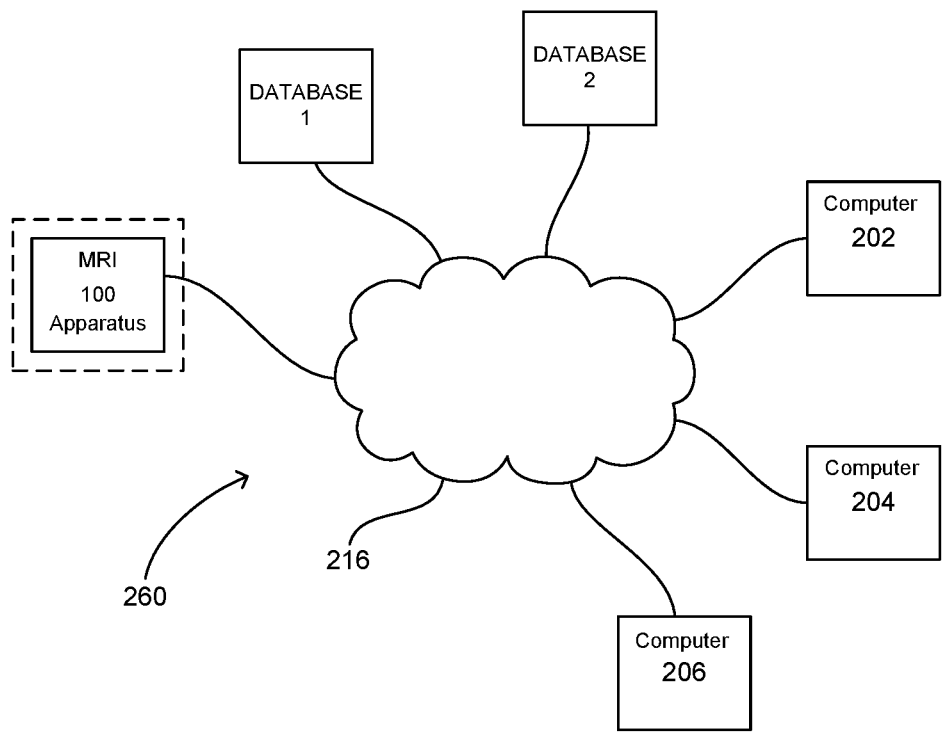
FIG. 2B illustrates a networked system in accordance with an aspect of this disclosure.

The system 200 may be part of a computer network as shown in FIG. 2B. The illustration of FIG. 2B presents a schematic diagram of a computer system depicting various computing devices that can be used alone or in a networked configuration in accordance with aspects of the invention. For example, this figure illustrates a computer network 260 having a plurality of computers 202, 204 and 206. The network 260 may include other types of devices such as mobile phones or PDAs. Various elements in the computer network 260 may be interconnected via a local or direct connection (such as shown in FIG. 2A) and/or may be coupled via a communications network 216 such as a local area network ("LAN"), a WiFi network, a wide area network ("WAN"), the Internet, etc. and which may be wired or wireless. The communications network 216 may include a plurality of nodes having routers, servers, wireless access points, etc.

Figure 2C:
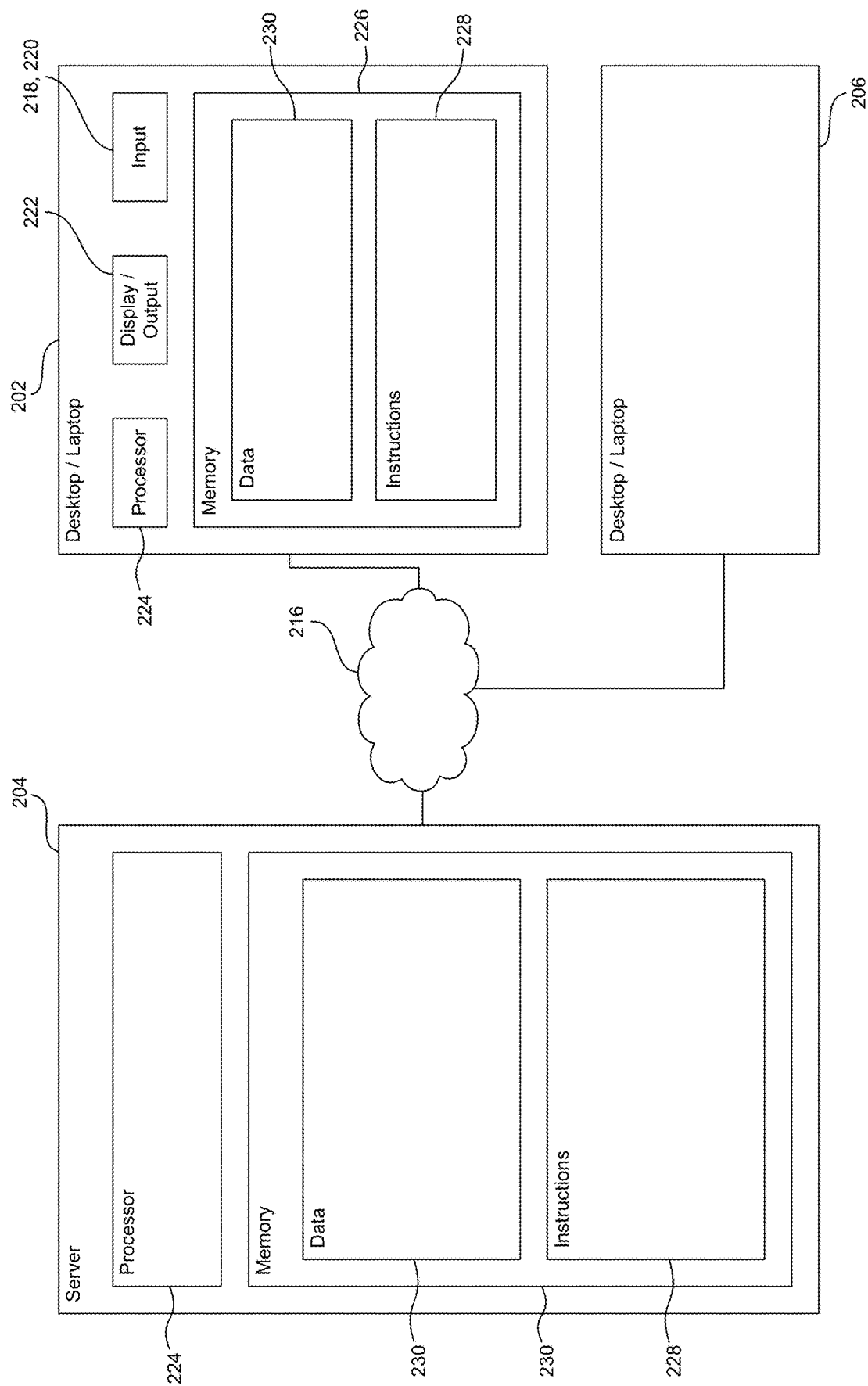
FIG. 2C shows computing devices that may be used in accordance with an aspect of this disclosure.

Each computing device can include, for example, one or more computers having user inputs such as a keyboard and mouse and/or various other types of input devices such as pen-inputs, joysticks, buttons, touch screens, etc., as well as a display, which could include, for instance, a CRT, LCD, plasma screen monitor, TV, projector, etc. Each computer 202, 204 and 206 may be a personal computer, server, etc. By way of example only, computer 202 may be a desktop computer, while computer 204 may be a server, and computer 206 may be a laptop. As shown in FIG. 2C each computer, such as computers 202 and 204, contains a processor 224, memory 226 and other components typically present in a computer.

With continued reference to FIG. 2C, memory 226 stores information accessible by processor 224, including instructions 228 that may be executed by the processor 224 and data 230 that may be retrieved, manipulated or stored by the processor. The memory may be of any type capable of storing information accessible by the processor, such as a hard-drive, ROM, RAM, CD-ROM, DVD, Blu-Ray disk, flash memories, write-capable or read-only memories. The processor 224 may comprise any number of well known processors, such as processors from Intel Corporation. Alternatively, the processor may be a dedicated controller for executing operations, such as an ASIC.

The instructions 228 may comprise any set of instructions to be executed directly (such as machine code) or indirectly (such as scripts) by the processor. In that regard, the terms "instructions," "steps" and "programs" may be used interchangeably herein. The instructions may be stored in any computer language or format, such as in object code or modules of source code. The functions, methods and routines of instructions in accordance with the present invention are explained in more detail below.

Data 230 may be retrieved, stored or modified by processor 224 in accordance with the instructions 228. The data may be stored as a collection of data. For instance, although the invention is not limited by any particular data structure, the data may be stored in computer registers, in a relational database as a table having a plurality of different fields and records, XML documents, or flat files. Map-type image data may be stored in flat files such as keyhole flat files ("KFF"). Content and advertising data may be stored in one or more relational databases.

The data may also be formatted in any computer readable format such as, but not limited to, binary values, ASCII etc. Similarly, the data may include images stored in a variety of formats such as vector-based images or bitmap images using lossless (e.g., BMP) or lossy (e.g., JPEG) encoding. Moreover, the data may include any information sufficient to identify the relevant information, such as descriptive text, proprietary codes, pointers, references to data stored in other memories (including other network locations) or information which is used by a function to calculate the relevant data.

Although the processor 224 and memory 226 are functionally illustrated in FIG. 2C as being within the same block, it will be understood that the processor and memory may actually comprise multiple processors and memories that may or may not be stored within the same physical housing or location. For example, some or all of the instructions and data may be stored on a removable recording medium such as a CD-ROM, DVD or Blu-Ray disk. Alternatively, such information may be stored within a read-only computer chip. Some or all of the instructions and data may be stored in a location physically remote from, yet still accessible by, the processor. Similarly, the processor may actually comprise a collection of processors which may or may not operate in parallel. Data may be distributed and stored across multiple memories 126 such as hard drives, data centers, server farms or the like.

In one aspect, the computing device 204 comprises a server. The other computing devices 202, 206 computer may be a general purpose computer, intended for use by a person, having all the components normally found in a personal computer such as a central processing unit ("CPU"), display, CD-ROM, DVD or Blu-Ray drive, hard-drive, mouse, keyboard, touch-sensitive screen, speakers, microphone, modem and/or router (telephone, cable or otherwise) and all of the components used for connecting these elements to one another.

The server and computers are capable of direct and indirect communication with other computers, such as over network 216. The network 216, including any intervening nodes, may comprise various configurations and protocols including the Internet, intranets, virtual private networks, wide area networks, local networks, private networks using communication protocols proprietary to one or more companies, Ethernet, WiFi, Bluetooth and HTTP.

Communication across the network, including any intervening nodes, may be facilitated by any device capable of transmitting data to and from other computers, such as modems (e.g., dial-up or cable), network interfaces and wireless interfaces. Server 204 may be an application server such as a web server.

Although certain advantages are obtained when information is transmitted or received as noted above, other aspects of the invention are not limited to any particular manner of transmission of information. For example, in some aspects, the information may be sent via a medium such as a disk, tape, CD-ROM, DVD, Blu-Ray disk or directly between two computer systems via a dial-up modem. In other aspects, the information may be transmitted in a non-electronic format and manually entered into the system.

The networked architecture 260 shown in FIG. 2B provides some flexibility in implementing the system. For example, the more complex processing may be done on the server 204, while the computer 202 may be used to control the actual acquisition of magnetic resonance signals from the apparatus 100. For example, the server may, in accordance with the discussions below, process the magnetic resonance signals it receives from computer 202 to identify the anatomy of interest and cerebro-spinal anatomy and then instruct the the computer 202 to perform measurements of the CSF using the identified anatomy of interest and cerebro-spinal anatomy. Alternatively, the system may be simplified architecturally as shown in FIG. 2A with only a computer, such as computer 204, more directly connected to the apparatus 100 and performing all the analysis, while at the same time controlling the apparatus 100.

Databases 1 and 2 are preferably used to store patient data, such as images resulting from MRI scans. The databases may also be used to store other data, as well as the computer code or instructions that the server and/or computers use to perform the measurements and methods disclosed herein.

In accordance with an aspect of the present invention, those measurements and methods include a software capability that detects and constructs outlines of anatomy of interest that allow for accurate and reproducible identification of anatomies of interest and measurement of CSF flow. Phase-contrast MRI pulse sequences provides the capability to visualize and measure the flow of CSF. The phase-contrast pulse sequence creates images with pixel intensities that correspond to flow rates. Conversion factors may be used to convert pixel intensity in MRI images into absolute CSF flow rates. In addition to flow rates, volume and pressure gradient of the CSF may also be computed based on the pixel intensity. Conventional programs rely on the user drawing outlines around the CSF to determine CSF flow. Using these programs it is often very difficult, at the very first level, to identify the outlines of the anatomical region of interest that defines the CSF flow channel. In addition, even where an inaccurate outline is drawn, it is not reproducible.

In a method in accordance with the present invention, a portion of the cerebro-spinal anatomy of a subject is selected for magnetic resonance imaging. The cerebro-spinal anatomy may include any one of the ventricles, the cerebral acqueduct (or acqueduct of Sylvius), spinal canal, the subarachnoid space, the epidural space, the cerebello-medullary cistern, foramen of Monro, foramen of Magendie, foramen magnum, etc., i.e., anywhere that CSF is flowing. Once the region of interest of the cerebro-spinal anatomy is selected, e.g., by a user, a phase contrast MRI pulse sequence is then acquired of the region using apparatus 100. Next, a center point or central location within the region of interest is identified. Using the center point or central location, the intensity of image pixels resulting from the phase contrast scan is then compared to intensity thresholds to determine the interior and exterior outlines of the region of interest bordering the CSF flow. Once the outlines are determined, the CSF flow can be determined using conversion factors that convert pixel intensity into flow rates for those pixels within the region defined by the outlines.

Figure 3:
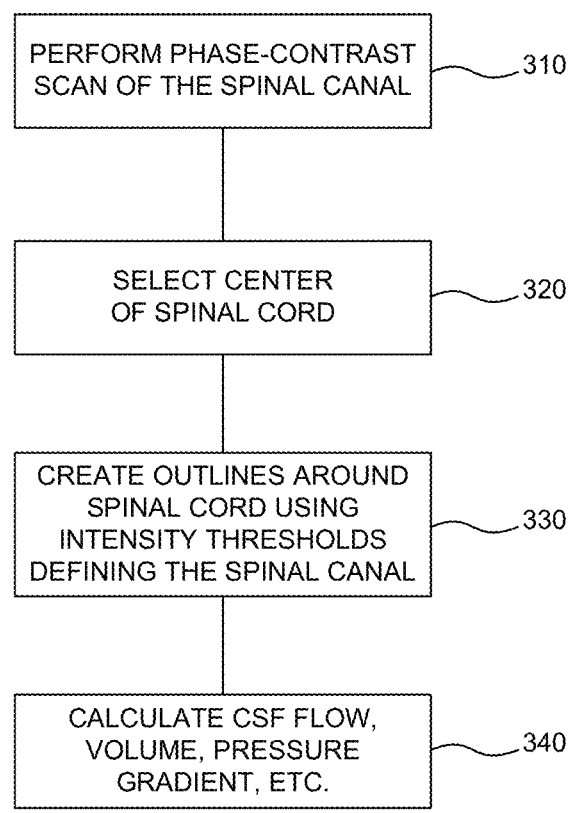
FIG. 3 shows method steps in accordance with an aspect of this disclosure.
Figure 4:
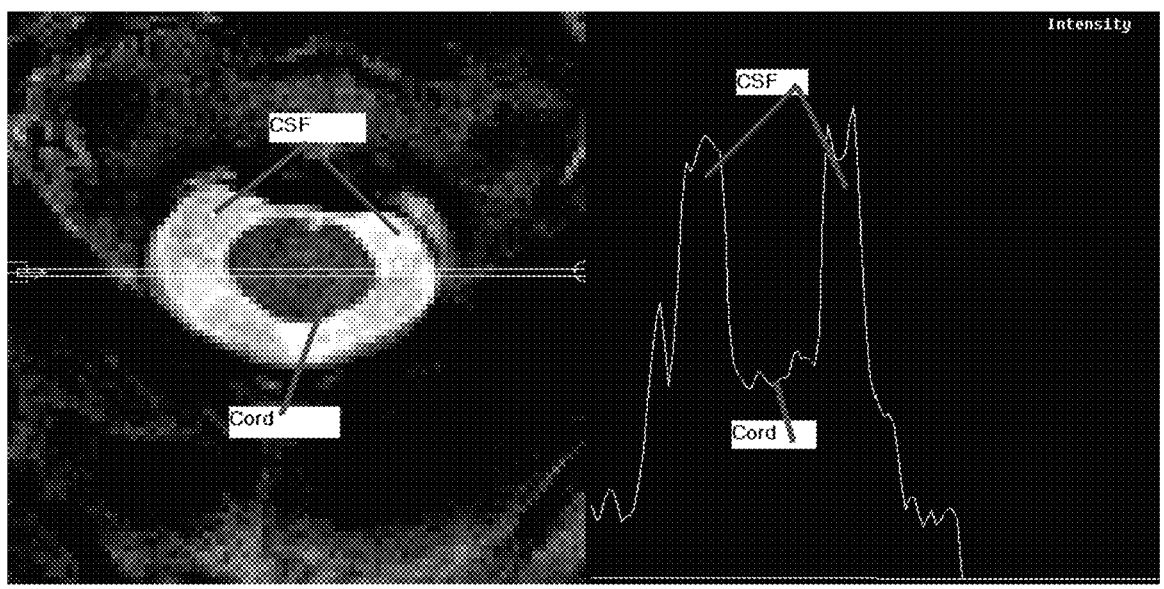
FIG. 4 shows a sample measurement made in accordance with an aspect of this disclosure.

In a more specific example as shown in FIG. 3, the method is explained with the region of interest being the spinal canal. Typically, these measurements are preferably made at the mid-C-2 vertebra of the spine, but may also be made elsewhere with appropriate modification. As explained above, the method begins with a phase-contrast pulse sequence scan of the spinal canal, block 310. Next, the center of the spinal cord is selected, block 320. This selection may be done by a user or preferably can be done via software using the intensity threshold algorithms described below. Next, based on pixel intensity thresholding, a first outline is created and placed around the spinal cord and second outline is created that defines the external border of the CSF region of the spinal canal, block 330. FIG. 4 shows an example of how intensity threshold is used to create outlines around the spinal cord and the surrounding CSF. The plot on the left corresponds to the outlines the designating the spinal cord and the CSF region. The plot on the right corresponds to the horizontal line in the left image.

Returning now to FIG. 3, once the outlines are created, they define a region that identifies the CSF. Once this region is identified, a phase contrast flow analysis uses the intensity values within the CSF region to calculate flow rates, velocity, volume and pressure gradient of the CSF, block 340. The details of the techniques for such an analysis may be found by reference to the following article, which is incorporated by reference herein: Sep. 20, 2011 paper entitled "The Possible Role of Cranio-Cervical Trauma and Abnormal C SF Hydrodynamics in the Genesis of Multiple Sclerosis" and published in Physiological Chemistry and Physics and Medical NMR, Vol. 41: 1-1. Such techniques involve a frame-by-frame motion analysis of pixels within a region. These measurements may be calculated and displayed soon after, e.g., from a few seconds to several minutes (10-15 minutes), the scan. Alternatively, they may be stored, e.g., in the databases mentioned above, and then later processed at the server or other computing device mentioned above.

In another aspect, the method may proceed as follows. An MRI technologist (MRI "tech") will first cursor "click" the center of the spinal cord in this example. Next, a first outline is created and placed around the spinal cord and a second outline is created that defines the external border of the CSF in the spinal canal. The outlines are preferably created automatically using software incorporating the methodology described herein. The two outlines will then define the CSF present in spinal canal. Sitting, "real time" at the MRI console the MRI "tech" will then position the MRI image "cursor" at the external border of the spinal canal and upon cursor activation ("cursor click") the magnetic resonance imaging system will measure and/or compute the CSF flow (cc/sec) and CSF velocity (cm/sec) of the CSF under examination, e.g., in this case inside the spinal canal. But the same measurement, under "tech" and cursor designation will then be "real time" measured in any CSF channel, e.g., the cerebral aqueduct. This will enable the measurement, real time CSF flow pre-op and immediately post-op to assure that the surgical procedures utilized, e.g., neuro-surgical, art-biopedic and neurologic have not compromised CSF flow. The CSF measurements are preferably made both in a recumbent and upright position. In accordance with this aspect of the invention, a computing device, such for example the desktop/laptop 202 of FIGS. 2B and 2C, would be configured to receive input from a user or "MRI tech." The input may include the user drawing anatomical outlines on the spinal anatomy that define, for example, the outlines of the spinal cord and CSF around the spinal cord. The desktop/laptop may then further process this input to determine the cross-sectional area defined by the outline, e.g., the area between the inner and outer borders shown in FIG. 4. Once the cross sectional area is determined (e.g., in units of $cm^2$) the CSF flow may be computed based on the cross-sectional area and a measure of CSF velocity within that area. The measure of CSF may be determined from a separately run scan, which measures the velocity or rate at which flow enters and exit, e.g., in cm/second, a predetermined cylindrical space surrounding the spinal cord. Thus, in accordance with this aspect once the input is received from a user, the software program (as described in further detail below) may thereafter perform the tasks for actual determination of CSF flow. As such, the process would begin with receipt of the user input by the software algorithm.

As discussed above, in one aspect the outlines defining the region of interest is done using software that carries out an intensity threshold algorithm. The software algorithm is colloquially referred to as the CSFROI program. In the case of the spinal canal, the algorithm uses a central point in the spinal cord, which is inside the region of interest on an axial view, to determine the outer and inner borders of the region of interest. It uses intensity thresholds to determine the interior and exterior CSF boundaries in a radial sweep around the central point in the cord. This works best on T2-weighted images because they provide high intensity pixels from CSF with low intensity pixels from the cord and other tissues. This algorithm uses a three-by-three pixel neighborhood average of the entire image to reduce the noise level. It also uses a three-by-three neighborhood average around the central cord point to obtain the mean cord intensity. The intensity threshold for interior region of interest is 50 percent above the cord's mean. The intensity threshold for the exterior ROI is 25 percent below the peak CSF intensity. These thresholds were determined empirically from patient studies with T2 and phase contrast axial images at the mid-C2 vertebra location. Intensity thresholds may vary depending the type of scan as well as the region of interest. The radial sweep steps by five degrees in a full 360 degrees around the central cord point. See FIG. 4 for a typical intensity profile.

A three-by-three neighborhood average smoothes out pixel intensities by averaging each value with its surrounding values. The "three by three" phrase describes the matrix dimensions around each pixel that was used for the average. This technique improves the Signal to Noise Ratio (SNR) at the expense of resolution. The resulting image will appear blurrier, but increases edge detection accuracy. An example of a three—by three average is as follows. Original pixel value and surroundings:

2 3 7

2 4 6

0 1 2

The central pixel value changes from 4 to the average value (2+3+7+2+4+6+0+1+2)/9=3. The same three-by-three average is used for the mean cord intensity. It is "around" the pixel that was clicked on with the mouse. Depending on the quality of the scan and type of scan, other averaging techniques may be used. For example, if the scan is noisier, a 4×4 thresholding technique may prove more useful. In contrast, a less noisier scan may use a 2×2 thresholding or no thresholding at all.

In general, the method can work on any other anatomy. However, because of variations in the shape, intensity, and signal to noise of other anatomy, the above parameters or algorithms may need to be modified. For example, for the CSF determination, the program uses a 50 percent increase to enter the CSF from the cord, and a 25 percent decrease to exit the CSF. These thresholds may differ for blood vessels. The edge detection algorithm for CSF may not work for more irregularly shaped objects, such as the ventricles. These changes may be determined empirical via MRI measurements or theoretically.

Other components of the system include an image display (IDS) program. The IDS program provides the user interface for identifying the CSF region and obtaining flow measurements. It allows for display of the T2 and phase-contrast images, preferably in stack mode. Stack mode involves looking at an image from each scan (or separate acquisitions) side-by-side, e.g., a T2 next to a phase contrast. It allows for identification of the central cord point on the T2. The IDS will create a data file with the image file name and central cord point's coordinates. The IDS will then run the CSFROI program with this input file. The CSFROI program determines the ROI points as described above and writes their coordinates to the same data file. The IDS then reads the ROI points and displays both ROIs. It then uses the ROIs to create a data file with information from the CSF pixel intensities in the phase-contrast image series. A phase contrast flow analysis (PCFA) program creates data files with the analysis results and produces a summary with the key measurements.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for detecting cerebrospinal fluid (CSF) flow of a subject, comprising:
    acquiring a plurality of magnetic resonance imaging signals of a selected region of interest of the subject's anatomy, the selected region of interest comprising a cerebro-spinal anatomy;
    receiving an indication of a central location of the cerebro-spinal anatomy, wherein the central location is in the subject's spinal cord;
    processing the acquired magnetic resonance imaging signals to determine a respective intensity value for each image pixel of a plurality of image pixels within the cerebro-spinal anatomy;
    determining a mean intensity value for the image pixels associated with the central location of the cerebro-spinal anatomy;
    determining an interior anatomical outline of the cerebro-spinal anatomy based on respective intensity values of image pixels outside of the central location exceeding the mean intensity value by at least a first threshold amount, wherein a perimeter of the interior anatomical outline encloses the central location on an axial view of the selected region of interest;
    determining an exterior anatomical outline of the cerebro-spinal anatomy based on the respective intensity values of image pixels outside of the central location being less than the mean intensity value by at least a second threshold amount, wherein a perimeter of the exterior anatomical outline encloses the interior anatomical outline on the axial view of the selected region of interest; and
    detecting the CSF flow between the interior and exterior anatomical outlines.

2. The method of claim 1, wherein the first threshold amount is 50%.

3. The method of claim 1, wherein the second threshold amount is 25%.

4. The method of claim 1, wherein the cerebro-spinal anatomy includes any one or combination of ventricles, cerebral acqueduct (or acqueduct of Sylvius), spinal canal, the subarachnoid space, the epidural space, the cerebello-medullary cistern, foramen of Monro, foramen of Magendie, and foramen magnum.

5. The method of claim 1, wherein determining each of the interior anatomical outline and the exterior anatomical outline is performed by evaluating image pixels outside of the central location in a sequence according to a radial sweep around the central location.

6. The method of claim 1, wherein acquiring the plurality of magnetic resonance imaging signals of the selected region of interest of the subject's anatomy is conducted while the subject is in an upright position.

7. The method of claim 6, wherein the upright position is selected from the group consisting of a sitting position and a standing position.

8. The method of claim 1, further comprising:
computing a measure of CSF velocity for the cross-sectional area based on the CSF flow detected between the interior and exterior anatomical outlines.

9. The method of claim 8, wherein the interior and exterior anatomical outlines define the subject's spinal canal.

10. The method claim 8, further comprising displaying the selected region of interest as an image on a display.

11. The method of claim 10, wherein the anatomical outlines are displayed on the display, and wherein the image on the display comprises the central location.

12. The method of claim 1, wherein determining the mean intensity value comprises calculating a three-by-three neighborhood average associated with image pixels of the central location, and wherein determining an intensity value of a given pixel comprises calculating a three-by-three neighborhood average of the given pixel.

13. A system for measuring cerebrospinal fluid (CSF) flow of a subject, comprising:
an apparatus for acquiring a plurality of magnetic resonance imaging signals of a selected region of interest of the subject's cerebro-spinal anatomy, the apparatus having a pair of magnetic poles spaced apart along a horizontal direction parallel to a support surface of the apparatus, the magnetic poles configured to create a magnetic field in the horizontal direction, the apparatus capable of accommodating the subject between the poles in an upright position;
a memory storing instructions;
a processor programmed using the instructions and configured to:
receive the acquired magnetic resonance signals,
receive an indication of a center location of the selected region of interest of the subject's anatomy, wherein the center location is in the subject's spinal cord,
for each given image pixel of a plurality of image pixels within the selected region of interest, determine an intensity value of the given pixel based on the acquired magnetic resonance signals,
calculate a mean intensity value associated with the center location,
determine an interior anatomical outline of the cerebro-spinal anatomy based on the intensity values of the given image pixels outside of the center location exceeding the mean intensity value by at least a first threshold amount, wherein a perimeter of the interior anatomical outline encloses the center location on an axial view of the selected region of interest,
determine an exterior anatomical outline of the subject's cerebro-spinal anatomy based on the intensity values of the given image pixels outside of the interior anatomical outline being less than the mean intensity value by at least a second threshold amount, wherein a perimeter of the exterior anatomical outline encloses the interior anatomical outline on the axial view of the selected region of interest, and
detect the CSF flow between the interior and exterior anatomical outlines.

14. The system according to claim 13, wherein the cerebro-spinal anatomy includes any one or combination of ventricles, cerebral acqueduct (or acqueduct of Sylvius), the spinal cord, spinal canal, the sub-arachnoid space, the epidural space, the cerebello-medullary cistern, foramen of Monro, foramen of Magendie, and foramen magnum.

15. The system according to claim 13, wherein the apparatus is configured to accommodate the subject in at least one of an upright sitting position and an upright standing position between the poles.

16. The system according to claim 13, wherein the processor is configured to:
determine the intensity value of the given pixel by calculating a three-by-three neighborhood average of the given pixel;
determine the mean intensity value by calculating a three-by-three neighborhood average associated with image pixels of the center location.

\* \* \* \* \*